US006363936B1

(12) United States Patent
McCormick et al.

(10) Patent No.: US 6,363,936 B1
(45) Date of Patent: Apr. 2, 2002

(54) STRAPPING DEVICE FOR PATIENT TRANSPORT

(75) Inventors: David A. McCormick, Gold Canyon; Rickey L. Salyers, Waddell; Martha S. McCormick, Gold Canyon, all of AZ (US)

(73) Assignee: 2Protectu, Inc., Gold Canyon, AZ (US)

( * ) Notice: Subject to any disclaimer, the term of this patent is extended or adjusted under 35 U.S.C. 154(b) by 0 days.

(21) Appl. No.: 09/454,523

(22) Filed: Dec. 6, 1999

(51) Int. Cl.[7] .................................................. A61F 5/37
(52) U.S. Cl. ............................... 128/870; 5/624; 5/625
(58) Field of Search ................................ 128/845, 869, 128/870; 5/624, 625, 627

(56) References Cited

U.S. PATENT DOCUMENTS 2,489,828 A * 11/1949 Springer ........................ 5/627
3,889,668 A * 6/1975 Ochs .......................... 128/870
4,124,908 A 11/1978 Burns et al. .................. 5/82 R
4,267,830 A 5/1981 Vick ........................ 128/87 R
4,679,260 A 7/1987 Frettem ....................... 5/82 R
5,435,323 A * 7/1995 Rudy ......................... 128/870
5,839,137 A * 11/1998 Butler ........................... 5/627
6,135,115 A * 10/2000 Rodarte ...................... 128/870

* cited by examiner

*Primary Examiner*—Michael A. Brown
(74) *Attorney, Agent, or Firm*—Gray Cary Ware & Freidenrich LLP; June M. Learn

(57) ABSTRACT

The invention provides inexpensive and disposable strapping devices for fixedly binding a supine subject to a rigid board, such as a body board. The invention strapping devices are adaptable to the girth and length of a subject in the range from about 40 pounds to 350 pounds, having straps of adjustable length and adjustable position along the length of the subject and are suitable for use with a subject whose head and/or neck is immobilized in a head block to prevent a potential shearing point at the neck of the subject. In another embodiment, the invention provides heavy duty reusable strapping devices for securely strapping a patient into a litter, such as a Stokes basket, for transport. The heavy duty litter strapping devices are adjustable to the size of the subject and are quick and easy to apply, but are of sufficient strength to be utilized in emergency rescue situations.

45 Claims, 4 Drawing Sheets

STRAPPING DEVICE FOR PATIENT TRANSPORT

FIELD OF THE INVENTION

The present invention generally relates to medical equipment, and more particularly to strapping devices used in patient transport.

BACKGROUND OF THE INVENTION

Many different types of devices are used for transport of injured patients depending upon the type of injuries involved and the environment from which the subject must be removed for transport to medical facilities. The degree and type of trauma is often determinative of the type of device to be used, and hence the means of transporting. For example, severe back or neck injuries require a body board to immobilize the patient subject. In the case of suspected head or neck injuries, the body board is equipped with a head block device to immobilize the head and neck regions of the patient, making these regions very secure. However, unless the remainder of the patient's body is immobilized in alignment with the head and neck there is a potential that the body will move even when strapped into a body board, creating a potential shearing point at the neck of the patient. The difficulties of this situation are considerably increased if the patient is very large and heavy because there may be an increased tendency for an obese patient to roll on the body board. Breakage of the strapping mechanisms in such cases is also a possibility.

To overcome some of these difficulties, there have been developed body boards provided with self-locking, releasable strapping means for holding a patient in a relatively fixed position on a body board or spine board having an attached head stabilizing device, such as are disclosed in U.S. Pat. No. 4,267,830.

However, during many patient transfers that utilize such a body board, potentially infectious biological fluids, such as blood and mucus, may contaminate the surfaces or soak into attached strapping devices, thereby increasing susceptibility to infection for occupants, as well as for medical practitioners and facility personnel. Washing or cleaning of patient bearing structures is possible, but manual cleaning often consumes valuable nursing time and also removes the patient bearing structure from service for an extended period of time. Further, manual cleaning may not be sufficiently reliable because contaminating stains are seldom completely eliminated, and thus the risk of transferring pathogens still exists.

In addition, in time of war or during emergency operations occasioned by fire, earthquake, flood and other natural disasters, the injured or dead need to be moved from sites that are inaccessible to ambulances and paramedic units. Similarly, in sports such as skiing, mountain climbing, and hiking, an accident may occur at a relatively inaccessible location, and removing the injured person may require specialized equipment and specially trained personnel. In many parts of the country, specially trained teams called technical rescue teams (TRT) are relied upon for patient transport in such situations. Strapping devices used by professionally trained TRT are required to meet rigorous tests of strength and durability.

Heretofore, such devices as stretchers, body boards, and Stokes baskets have been used to remove the patient from the scene. In the case of stretchers, litters and body boards, at least two, and preferably four, people are required to transport the stretcher or board and the patient. The Stokes basket can be transported by hand, but is also designed to be lifted and transported by a helicopter, or, when used at sea, by an arrangement similar to a breeches buoy, for transfer between ships. During such rescues it is extremely important that the injured subject not be allowed to roll or fall out of the transport device.

Accordingly, there is still a need in the art for strapping devices for securing a subject to a body board or litter that are separate from the board. In addition, inexpensive, preferably fluid resistant and/or disposable strapping devices are needed. Additionally, a need exists for strapping devices that will effectively immobilize the body of a patient whose head is secured in a head stabilization device, such as a cervical collar, and for strapping devices of sufficient strength to be utilized in emergency rescue situations.

BRIEF DESCRIPTION OF THE INVENTION

The present invention overcomes many of the problems in the art by providing strapping device(s) for fixedly, but releasably binding a supine subject to a rigid board. The invention devices are especially useful for immobilizing the body (e.g., torso and legs ) of a patient whose head is immobilized by insertion into a head block or stabilization device, such as a cervical collar, that is fixedly attached to the rigid board. The invention strapping devices are not permanently affixed to any type of body board or other transport device and are designed to be either inexpensive to manufacture and disposable or reusable and of sufficiently high strength design to meet or exceed all rescue standards.

Therefore, in one embodiment of the present invention, there are provided strapping device(s) for fixedly binding a supine subject to a rigid board. The invention strapping devices comprise at least two lengthwise adjustable longitudinally extending straps having head ends and leg ends, and shoulder points and being fixedly secured together at the leg ends and shoulder points. The invention strapping devices further comprise bilaterally extending straps being attached in pairs to the longitudinally extending straps, with the pairs at the shoulder points and leg ends being fixedly attached, and additional pairs being attached to the longitudinally extending straps in spaced apart longitudinal relation between the leg ends and shoulder points and cinching fasteners attached to free ends of the bilaterally extending straps for fixedly, but releasably binding the subject to the rigid board.

In another embodiment of the present invention, there are provided strapping device(s) for strapping a supine patient into a litter with attachment points. The invention litter strapping device comprises (1) at least two longitudinally extending straps, each having a head end, a foot end, and a shoulder point and being fixedly fastened together at the leg ends and shoulder points, (2) bilaterally extending straps being attached by pairs to the longitudinally extending straps via slide fasteners and fixedly attached to the leg ends and shoulder points of the longitudinally extending straps, (3) buckles attached to the longitudinally extending straps and bilaterally extending straps for adjusting the effective length of the straps, and (4) locking fasteners attached to the longitudinally extending and bilaterally extending straps for releasably securing the straps to the attachment points of the litter.

DETAILED DESCRIPTION OF THE INVENTION

Figure 1:
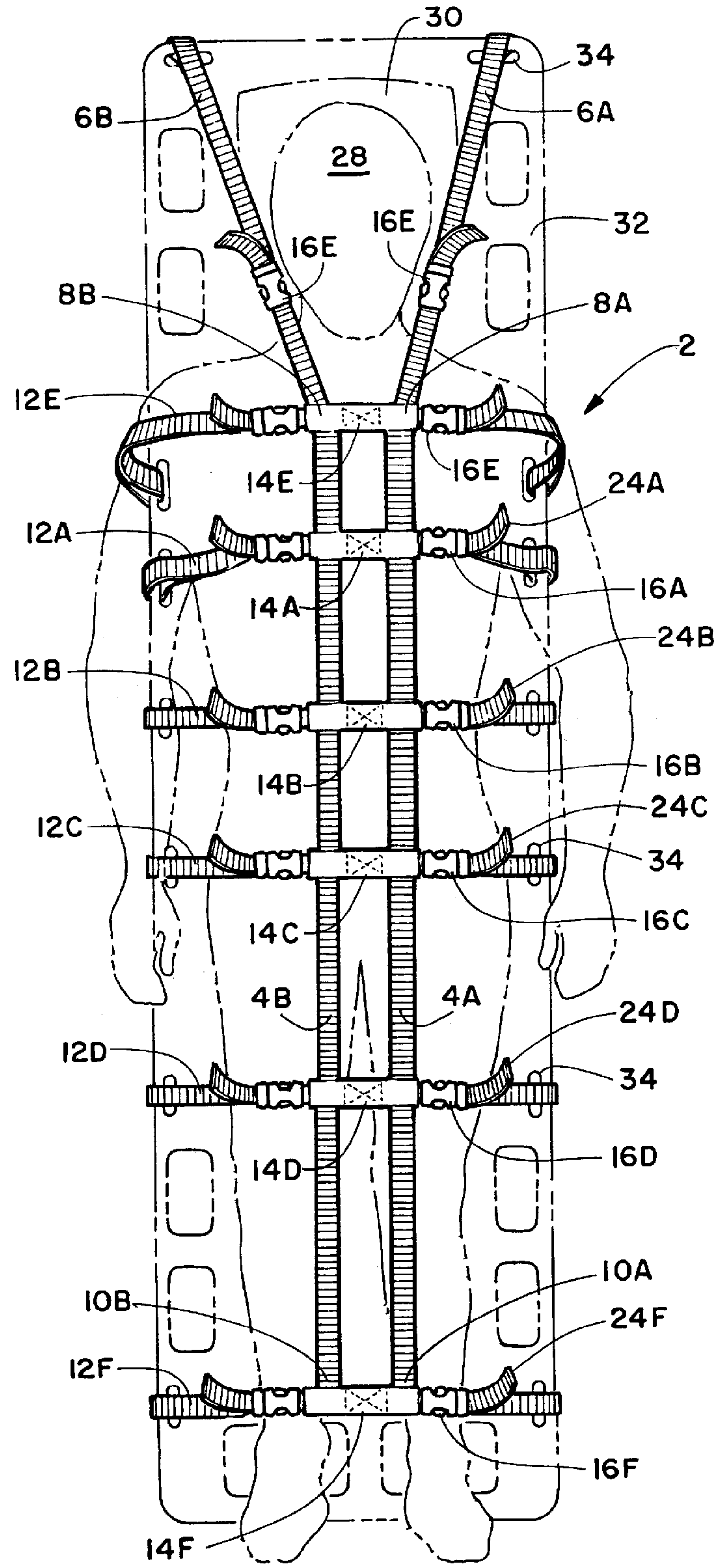
FIG. 1 is a drawing showing a subject with head in a head block and who is strapped to a body board by means of an invention strapping device.

In accordance with the present invention, there are provided strapping device(s) for fixedly, but releasably binding a supine subject to a rigid board. However, the invention strapping devices are not permanently affixed to any type of body board and are designed to be inexpensive to manufacture and disposable in many embodiments.

The invention strapping devices comprise at least two lengthwise adjustable longitudinally extending straps having head ends, leg ends, and shoulder points, and being fixedly secured together at the leg ends and shoulder points, wherein the distance between the head ends and the shoulder points on the longitudinally extending straps is adjustable. The invention devices further comprise bilaterally extending straps being attached in pairs to the longitudinally extending straps, with the pairs at the shoulder points and leg ends being fixedly attached, and additional pairs being attached to the longitudinally extending straps in spaced apart longitudinal relation between the leg ends and shoulder points. Cinching fasteners attached to free ends of the bilaterally extending straps are adapted to fixedly, but releasably bind a subject to a rigid board.

The device is designed to be applied over a subject after the subject has been placed on the body board without the need to move or roll the body about. Therefore, the device is adapted to being passed over the subject supine on the board with the longitudinally extending straps attaching to the board at the head ends thereof, and the bilaterally extending straps being adapted to be passed around the subject and the rigid board and fastened together by cooperatively engaging the cinching fasteners. The longitudinally extending straps can be made adjustable between the head ends that attach to the board and the shoulder point by any means known in the art, such as a cinching fastener.

It is presently preferred that the pairs of bilaterally extending straps between the shoulder points and leg ends of the longitudinally extending straps are slideably attached thereto via slide fasteners so that the positioning of the bilaterally extending straps along the torso of the patient is adjustable, thereby allowing for the strapping device to be tailored to the stature and longitudinal dimensions of the patient. Slide fasteners used for attachment of the bilaterally extending straps to the longitudinally extending straps can be of a number of different types. For example, the slide fasteners can be rings that are slipped over the longitudinally extending straps and to which the slideable bilaterally extending straps are attached by passing through the rings and fastening to themselves. Alternatively, pieces of material, such as the straps are made of, referred to herein as "spacer pieces," can be self-attached in a ring around the longitudinally extending straps while remaining free to slide along the longitudinally extending straps. In any event, the slideable bilaterally extending straps are then attached by pairs to the slide fasteners. Preferably, the slide fasteners are spacer pieces that lie flat against the torso of the injured subject and are adapted to avoid bunching of the longitudinally extending straps together, preferably allowing for some distance between the at least two longitudinally extending straps along the torso of the subject.

The invention strapping device is designed to be applied to the supine patient in the following manner. First, the head ends of the longitudinally extending straps are attached to the head of the board. If the board is of the type that has a slot(s) at the head through which straps can be threaded to bind the strapping device to the board, it is preferred that the head ends of the longitudinally extending straps have releasably engageable cinching fasteners and that the head ends of the longitudinally extending straps are long enough to be threaded through the cinching fastener, loop through the slot at the head end of the board and then pass back through the cinching fastener to attach the head ends of the longitudinally extending straps to the head end of the board. The distance between the head ends of the longitudinally extending straps and the shoulder points thereof can then be adjusted using the cinching fasteners as needed to place the shoulder points at the shoulders of the patient. Next, the cinching fasteners on the pairs of bilaterally extending straps attached to the leg ends and shoulder points of the longitudinally extending straps are operated as described above to attach the strapping device to the body board and the effective length of the straps is adjusted to bind the shoulders and lower legs of the patient to the board.

The remainder of the pairs of bilaterally extending straps, which are slideably attached to the longitudinally extending straps, can be distributed over the torso and thigh and leg regions of the patient in spaced apart relation to distribute the pressure exerted on the patient by the strapping device over several points. Then the remainder of the pairs of bilaterally extending straps are attached to the board and tightened to adjust the effective lengths thereof as described above.

To aid in application of the strapping device to a subject lying upon a board, the invention device is preferably marked with a set of legends or symbols indicating points of proper placement of the pairs of slideable bilaterally extending straps along the length of the subject to be strapped to the board. For example, if the pairs of bilaterally extending straps are slideably attached to the longitudinally extending straps via a number of individual slideable spacer piece, the spacer pieces provide a convenient place for marking the device with a set of legends or symbols indicating points of proper placement of the pairs of the attached bilaterally extending straps along the length of the subject to be strapped to the board. Generally, each legend or symbol identifies only one of the slideable spacer pieces and attached bilaterally extending straps for placement at or about the chest, abdomen, pelvis or thigh region of the subject. Additional appropriate legends or symbols can be placed on fixed spacer pieces at the shoulders and leg ends. Alternatively, the legends or symbols can be placed directly on the pairs of bilaterally extending straps and/or on the head and leg or foot ends of the longitudinally extending straps to aid in use of the invention strapping device.

In one embodiment according to the present invention, the strapping device is designed for binding a patient to a rigid board with side railings or a plurality of spaced apart slots located pairwise along opposite sides of the board. In this embodiment, the pairs of bilaterally extending straps and attached cinching fasteners are adapted to be threaded through the side railings or a corresponding pair of slots in the board with each bilaterally extending strap being fastened taut to itself by cooperative engagement of the attached releasably engageable cinching fastener so as to adjust the effective length of the strap and bind the subject to the board. For use with a rigid board provided with a head railing or head slot at the head portion thereof, the longitudinally extending straps of the invention device can be adapted to be threaded through the head railing or slot and fastened taut to themselves by the releasably engageable cinching fastener.

The invention strapping device is adapted for use in combination with a patient head block device that is fixedly attached to the rigid board (i.e., a body board) to immobilize the head and/or neck of the subject, such as a cervical collar, a Keds board, a vacuum splint, and the like. Because the head ends of the longitudinally extending straps are lengthwise adjustable, they are adapted to fasten to the head end of the board and run along on either side of the head block device into which the subject's head is placed for immobilization. The strapping device is applied to the body of the supine subject lying on the board and whose head is in the head block by adjusting the attaching hardware (i.e., cinching fasteners and/or buckles) so as to immobilize the remainder of the body of the subject in alignment with the immobilized head and/or neck.

The cinching fasteners used in the invention device can be of any type (e.g., commercially available) that is useful for fastening the subject to the rigid board on which it is supine. The cinching fasteners are preferably of the type that is quick and easy to engage and release (i.e. "releasable engageable") and also provides the operator with the ability to adjust the effective length of the strap to which it is attached. The "effective length" of a strap is the portion of the strap that is actively engaged in binding the subject to the rigid board or litter and is distinguished from the surplus part of the strap (also referred to herein as the free end of the strap) that is available for use if the operator desires to increase the effective length of the strap.

Side release snap fasteners, which are commonly used on backpacks, luggage, and the like, are the preferred type of cinching fastener for use in manufacture of the invention strapping devices. Usually side release snap fasteners are in two parts with a buckle portion attached to one part through which the strap passes so that the effective length of the strap is adjusted simply by pulling on the free (i.e., surplus) end of the strap, much as in an airline seat buckle. A friction-fit of the strap in the cinching fastener or teeth in the buckle portion of the side release snap fastener sets the strap at the new position and the tighter the strap is pulled against the subject on the board, the stronger the set of the strap in the cinching fastener becomes.

The cinching fasteners can be made of any material of sufficient strength to withstand cinching of the subject to the board. Examples of suitable materials for use in manufacture of the cinching fasteners used in manufacture of the invention strapping device include various types of plastics, polymers and metals, for example, polypropylene, nylon, steel, aluminum, and the like. Materials suitable for use as the straps in the invention strapping devices include such materials as polypropylene, canvas, cotton, or nylon webbing, and the like.

FIG. 1 is a drawing showing a subject 28 whose head is immobilized in a head block 30 and who has been strapped to a rigid body board 32 that is provided with slots 34 for receiving the straps of strapping device 2. In the embodiment of the strapping device shown in FIG. 1, strapping device 2 has two lengthwise adjustable longitudinally extending straps 4A–B with head ends 6A–B, shoulder point 8A–B and leg ends 10A–B. Four pairs of slideable bilaterally extending straps 12A–D are slideably attached to the longitudinally extending straps 4A–B using spacer pieces 14A–D as slide fasteners. Pairs of bilaterally extending straps 12A–D are attached to spacer pieces 14A–D through cinching fasteners 24A–D. Spacer pieces 14A–D are slideable along the portion of the longitudinally extending straps 4A–B between the shoulder points 8A–B and leg ends 10A–B thereof and also serve to prevent the longitudinally extending straps from either bunching together or from sliding off the to the side of a subject to which the device is applied. The longitudinally extending straps 4A–B are attached together at shoulder points 8A–B and at leg ends 10A–B by additional fixed spacer pieces 14E–F, with two additional pairs of bilaterally extending straps 12E–F with attached cinching fasteners 16*e–f* attached to each fixed spacer piece 14E–F.

Figure 2:
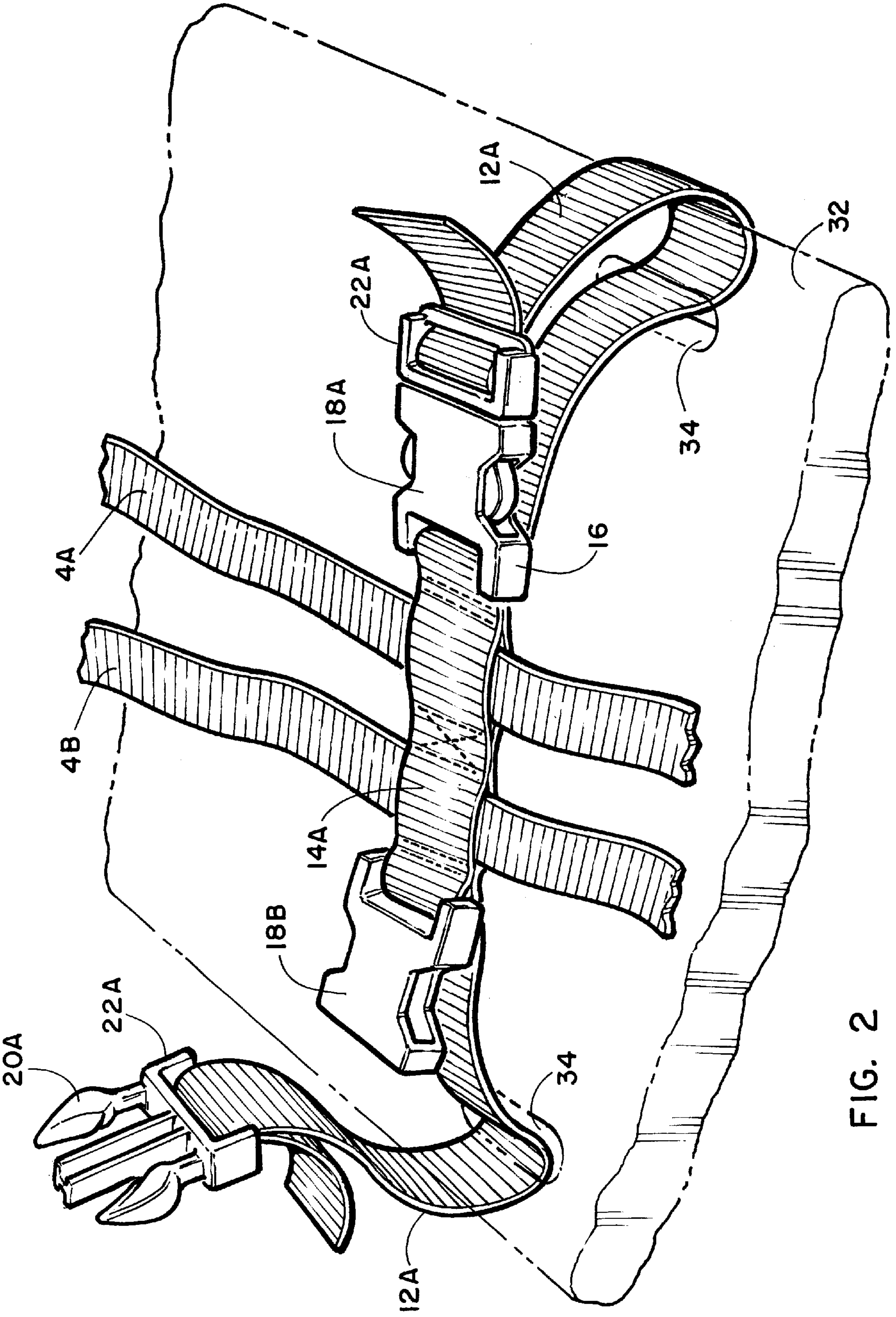
FIG. 2 is a detail of the assembly of the shoulder and chest area of the strapping device of FIG. 1 showing a fixed spacer piece and a slideable spacer piece, each having an attached pair of bilaterally extending straps with cinching fasteners. Operation of the device for attachment to a body board is also shown.

FIG. 2 shows in detail the assembly of one of the slideable spacer pieces and operation of the cinching fasteners in strapping device 2. Spacer piece 14A is shown with attached pair of cinching fasteners 16A–B and bilaterally extending straps 12A–B Cinching fasteners 16A–B are side release snap fasteners having a female side 18B and a male side 20B with a buckle portion 22B incorporated into the female side of the fastener. The female side 18B of the cinching fastener 16B is fixedly attached to the top side (as shown in FIG. 2) of spacer piece 14A. Immediately under the female side 18B of cinching fastener 16B, the bilaterally extending strap 12B is fixedly attached at one end (i.e., the attached end thereof) with the other end left free i.e., the free end 24B thereof).

In strapping device 2, the bilaterally extending straps are attached in opposing pairs to the slideable spacer pieces 14A–D and to the fixed spacer piece 14E at the jointure of the leg ends 10 (e.g., to the under sides of the spacer pieces). The head ends 6A–B of longitudinally extending straps 4A–B also are provided with cinching fasteners 16*f*, each having a buckle used for attaching the head ends of longitudinally extending straps to slots 34 located at the head end of body board 32. As is also shown in detail in FIG. 2, the free end 24*a* of the bilaterally extending strap 12*a* is adjustably attached to the male sides 20 of cinching fasteners 16 by threading through buckle portions 22 thereof.

Strapping device 2 is applied to body board 32 as follows. As shown in FIG. 2, with the cinching fasteners disengaged, the free end of a strap with attached male portion of the cinching fastener is individually threaded through an adjacent slot 34 in body board 32, the male and female portions of the cinching fastener are engaged, and the free end of the strap is pulled by the operator to adjust the effective length of the strap as needed to bind subject 28 to body board 32. This procedures is followed for each longitudinally extending strap 4A–B and pairs of bilaterally extending straps 12A–E. Preferably, this procedure of adjusting the effective length of the longitudinally extending and bilaterally extending straps is done by pairs to assure symmetry of the strapping device with respect to the midline of the subject's body. The pairs of bilaterally extending straps, which are slideably attached to the longitudinally extending straps via the spacer pieces are distributed over the torso, thigh and leg regions of the patient in spaced apart relation as indicated on legends 36 printed on the upper side of the spacer pieces. The head and leg ends of the longitudinally extending straps also bear legends 36 indicating the appropriate orientation of the invention strapping device with respect to body board 32 and the supine subject 28 thereon.

The overall dimensions of the invention strapping device are quite variable depending on the size of the patient with which it is designed to be used. Since in many embodiments the longitudinally extending straps and bilaterally extending straps are adjustable in length, it is contemplated that the invention strapping device can be used to bind patients in the weight range from about 40 pounds to about 320 or 350 pounds to a rigid body board for transport and/or immobilization.

It is presently preferred that the invention strapping device is designed to be strong, yet inexpensive to manufacture and, hence, disposable after a single use to avoid the problems inherent with contamination of the device by bodily fluids of injured or sick patients. The straps of disposable strapping devices are preferably made of polypropylene or nylon. The cinching fasteners in disposable strapping devices are generally made of polypropylene or nylon.

The legends or symbols can be attached to the straps of the device by any convenient means (e.g. by sewing, gluing, and the like) or placed directly onto the straps (e.g., stenciled, printed or appliqued) to aid in rapid application of the strapping device to the patient by rescue personnel. (For example, if the spacer pieces are made of a light colored material, it is convenient to stencil the legends or symbols onto the spacer pieces to indicate the proper spacing and location of the bilaterally extending straps along the torso of the patient's body.) It is particularly helpful in rapid application of the invention strapping device to have the head and leg ends of the device marked and identified in this way to aid the operator in orienting the device with respect to the supine subject before any attempt is made to begin securing the patient to the board by manipulating the various cinching fasteners.

Any of the invention devices can be manufactured of materials that provide sufficient strength to meet the requirements of apparatus used by a technical rescue team (TRT) for emergency transport of an injured person. Since apparatus used by a technical rescue team is required to have tensile strength in a 15:1 ratio to the patient's body weight, the straps in invention strapping devices that are designed for use by a TRT are made of materials having a tensile strength in the range from about 2150 to 2700 pounds, such as a nylon webbing rated as having such a strength. In addition, in such devices, the stress-bearing hardware, such as the cinching fasteners, buckles and/or locking fasteners are required to have equivalent strength or greater. Therefore, metal hardware is generally used in such devices, preferably steel or aluminum hardware.

In another embodiment of the present invention, the strapping device is designed for securing an injured person into a litter having at least one railing around the perimeter, such as a Stokes basket. Such litters are used for removal of injured persons from a location inaccessible to a gurney and/or ambulance, such as a cliff, deep trench, snowy slope, and the like. A Stokes basket generally has an upper and a lower railing surrounding the perimeter of the basket to keep the patient from falling out. The upper railing is used for attachment of suspension cables when such apparatus as a helicopter or a winch is used during transport of the patient, and the lower railing is used for strapping the patient into the Stokes basket.

Accordingly, in this embodiment, the invention provides a litter strapping device for strapping a supine patient into a litter with attachment points. Such a litter strapping device comprises:

at least two longitudinally extending straps, each having a head end, a foot end, and shoulder points, being fixedly fastened together at the foot ends and shoulder points, pairs of bilaterally extending straps being fixedly attached to the foot ends and shoulder points of the longitudinally extending straps, pairs of bilaterally extending straps being attached between the foot ends and shoulder points of the longitudinally extending straps via slide fasteners, buckles attached to the longitudinally extending straps and bilaterally extending straps for adjusting the effective length of the straps, and locking fasteners attached to the longitudinally extending and bilaterally extending straps for releasably securing the straps to the attachment points of the litter. Thus, the invention litter strapping device is adapted to secure a subject placed within the litter for secure transport.

In use, the invention litter strapping device is placed along the body of a subject placed within a litter (e.g., a Stokes basket) with the head and leg or foot ends oriented to correspond to those of the subject and with the bilaterally extending straps appropriately distributed along the body of the subject (e.g, at the subject's chest, abdomen, pelvis, and thigh regions). The locking fasteners are then fastened to the railing of the litter while the effective lengths of the various straps are adjusted to assure the safety and comfort of the subject.

Generally, at least four pairs of the bilaterally extending straps are slideably attached to the longitudinally extending straps. The pairs of straps can be slideably attached by any type of slide fastener, such as a ring threaded onto the longitudinally extending straps or via an individual slideable spacer piece slideably mounted on the longitudinally extending straps between the foot ends and the shoulder points, as disclosed more fully above. Further spacer pieces are optionally fixedly attached to the longitudinally extending straps at the foot ends and the shoulder points, each having a pair of the bilaterally extending straps attached thereto.

Optionally, at least one of the locking fasteners is attached to the foot end of the longitudinally extending straps via one or more intervening foot straps. The device may also optionally further comprise lengthwise adjustable foot loops attached to the longitudinally extending straps at/or near the foot/leg end thereof for receiving the feet of the patient and/or lengthwise adjustable shoulder loops attached to the longitudinally extending straps adapted for securing about the shoulders of the subject (as shown in FIG. 3 herein), for example by means of a cinching fastener as described hereinabove.

The locking fasteners in the invention litter strapping device are adapted to attach to the attachment points on the litter. For example, if the litter is a Stokes basket, which has an upper and lower railing surrounding the perimeter of an open mesh basket, the locking fasteners are adapted to fixedly, but releasably attach around the railing of the litter (e.g., the lower railing of a Stokes basket). Preferred locking fasteners are heavy duty hook and latch fasteners (of the type commonly used in parachute rigging) that are rated at over 3500 pounds of tensile strength. Preferably the strap is passed through a slot in the hook and latch fastener to create a loop that is lengthwise adjustable by means of a buckle fixedly attached to a longitudinally extending strap or to a spacer piece. The preferred type of buckle is one by which the effective length of the strap can be adjusted by pulling on a free (i.e., surplus) end of the strap, such as a parachute grade fastener.

The invention litter strapping device is also preferably marked with a set of legends or symbols indicating points of proper placement of the pairs of slideable bilaterally extending straps along the length of the subject to be strapped into the litter. For example, each pair of bilaterally extending straps can be slideably attached to the longitudinally extending straps via an individual slideable spacer piece, as described more fully above. Such spacer pieces provide a convenient place for marking the litter strapping device with a set of legends or symbols indicating points of proper placement of the pairs of slideable bilaterally extending straps along the length of the subject to be strapped into the litter, generally with each legend or symbol identifying only one of the slideable spacer pieces and attached bilaterally extending straps for placement at or about the shoulders, chest, abdomen, pelvis, thigh and feet regions of the subject. Additional appropriate legends or symbols can be placed on fixed spacer pieces. Alternatively, the legends or symbols can be placed directly on the pairs of bilaterally extending straps and/or on the head and foot ends of the longitudinally extending straps to aid in use of the invention litter strapping device.

Figure 3:
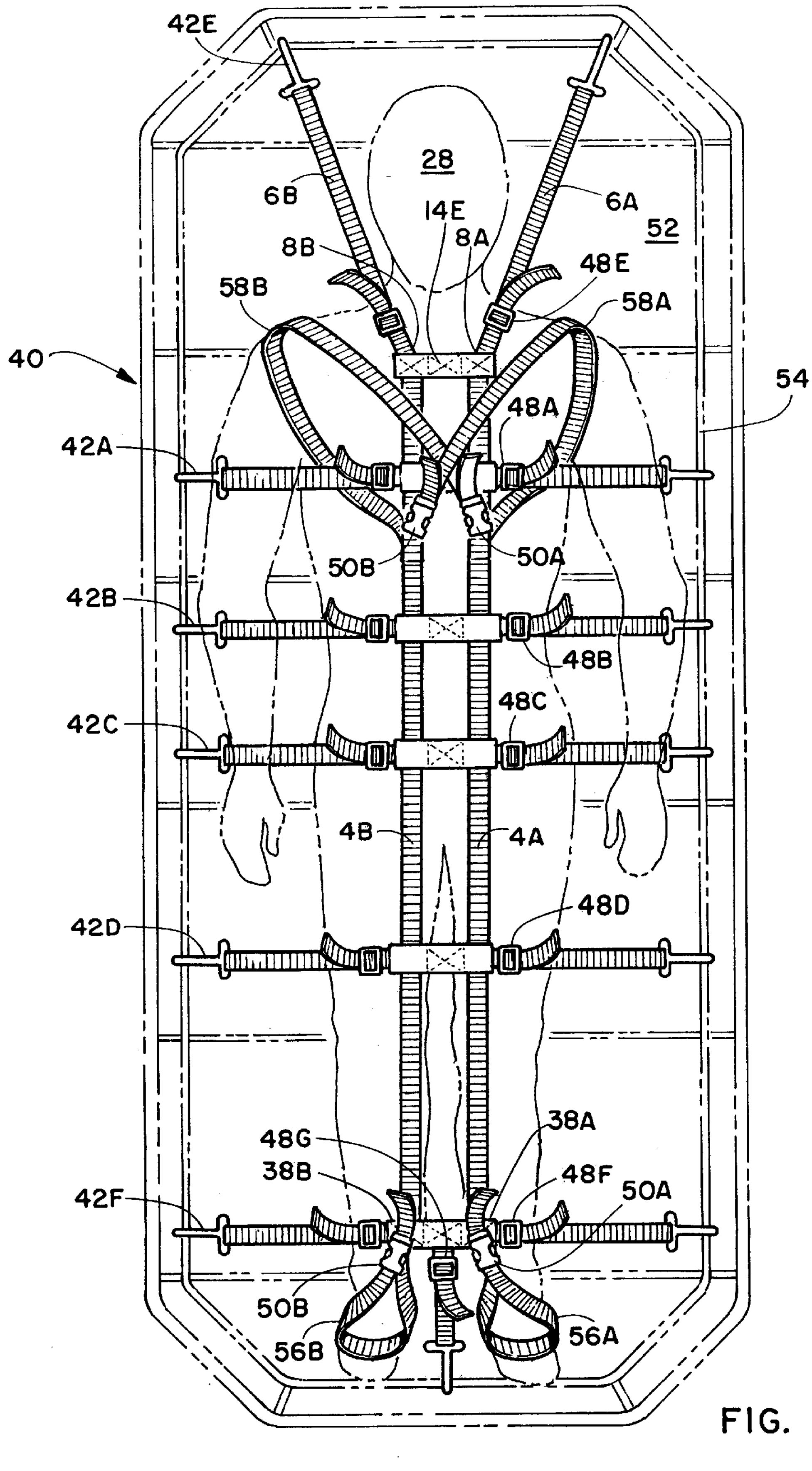
FIG. 3 is a drawing showing a subject strapped into a Stokes basket by means of an invention litter strapping device.

FIG. 3 is a drawing showing a preferred embodiment of the invention litter strapping device 40 designed for use with a litter, such as a Stokes basket, wherein the attachment points are located along a railing surrounding the perimeter of the basket. Litter strapping device 40 has two lengthwise adjustable longitudinally extending straps 4A–B with head ends 6A–B, shoulder points 8A–B and foot ends 38A–B. Four pairs of bilaterally extending straps 12A–D are slideably attached to the spacer pieces 14A–D via buckles 48A–D. The longitudinally extending straps 4A–B are attached together at shoulder points 8A–B and at foot ends 38A–B by additional fixed spacer pieces 14E–F, with an additional pair of bilaterally extending straps 12E attached to fixed spacer piece 14E. Each of the longitudinally extending straps and bilaterally extending straps has a buckle 48A–F and a locking fastener 46A–F mounted thereon. Each of the spacer pieces may be marked with a legend (not shown in this Figure) to indicate proper placement relative to the body of subject 28. As in the other embodiments, the spacer pieces 14 prevent the longitudinally extending straps from either bunching together or from sliding off the to the side of a subject to which the litter strapping device is applied.

Figure 4:
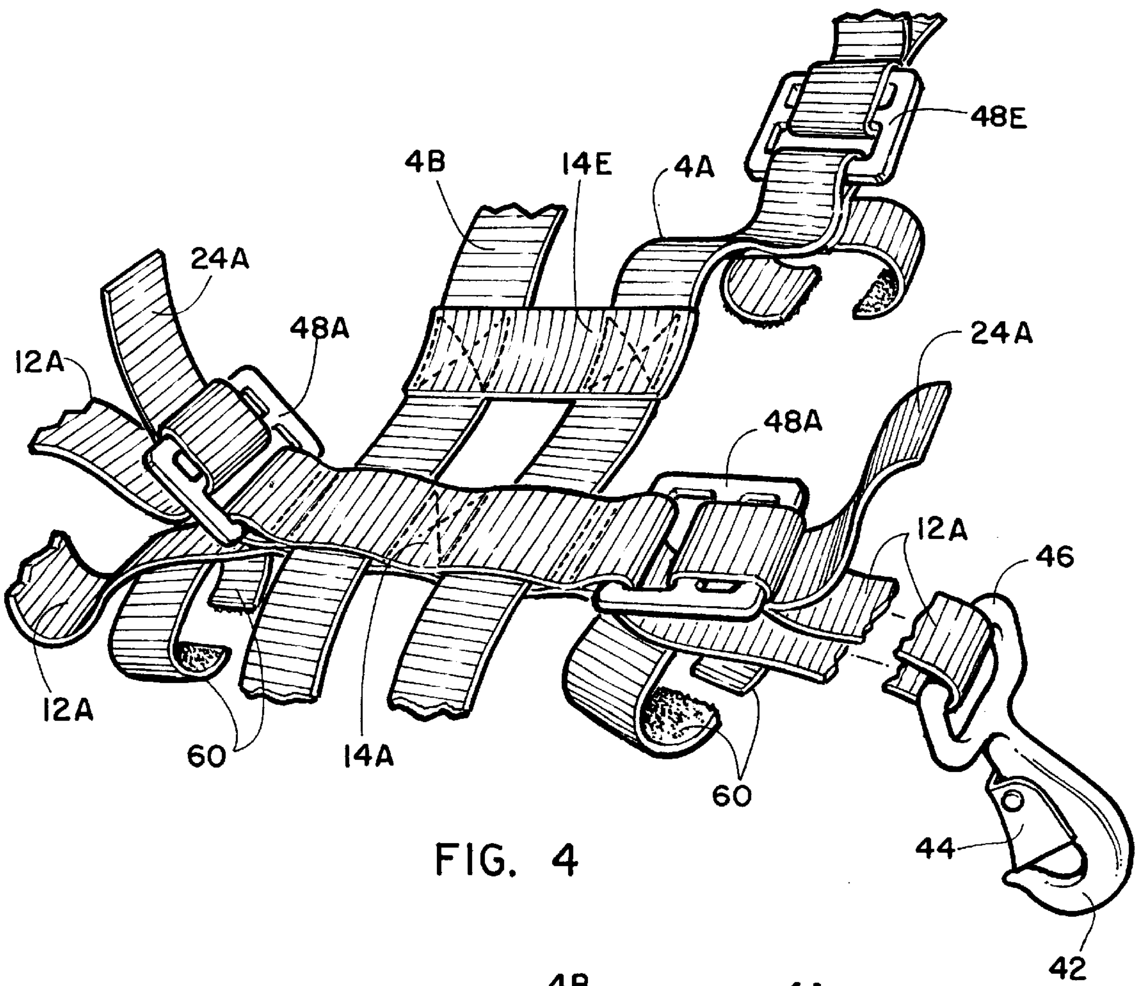
FIG. 4 is a detail of the assembly of the shoulder and chest area of the litter strapping device of FIG. 3 showing longitudinally extending straps with a fixed spacer piece at the shoulder point and pair of attached bilaterally extending straps and a slideable spacer piece at the chest area with attached bilaterally extending straps. Fastening hardware is shown attached to the bilaterally extending straps.

FIG. 4 shows in detail the assembly of the upper end of strapping device 40 with fixed spacer piece 14E and slideable spacer piece 14A attached to longitudinally extending straps 4A–B. Also shown in FIG. 4 are hook and loop containment strips 60 (in open position) attached to each of the straps. For convenience in application of the strapping device 40 (e.g., to avoid self-entanglement of the straps) each strap can be folded up and held in the folded-up position by fastening the containment strip 60 into a closed position around the respective folded strap until needed for use. A containment strip is easily moved into the open position by the operator pulling the hook and loop portions of the containment strip apart, thus freeing its respective contained strap for use.

Cinching fasteners 50A–B are attached to longitudinally extending straps 4-A–B as described above for adjusting the length of the longitudinally extending strap, but as further shown in FIG. 4, the pair of bilaterally extending straps 14A are attached to spacer piece 14A via a pair of buckles 48A through which the respective strap is threaded, leaving free end 24*a*. In addition, each of straps 14*a* has a locking fastener 42*a* (only one of the pair is shown) threaded thereon by passage of the free end 24*a* of bilaterally extending strap 12*a* through slot 46*a* of the locking fastener 42*a* (which is shown as a hook and latch fastener) before threading free end 24*a* through its respective buckle.

Figure 5:
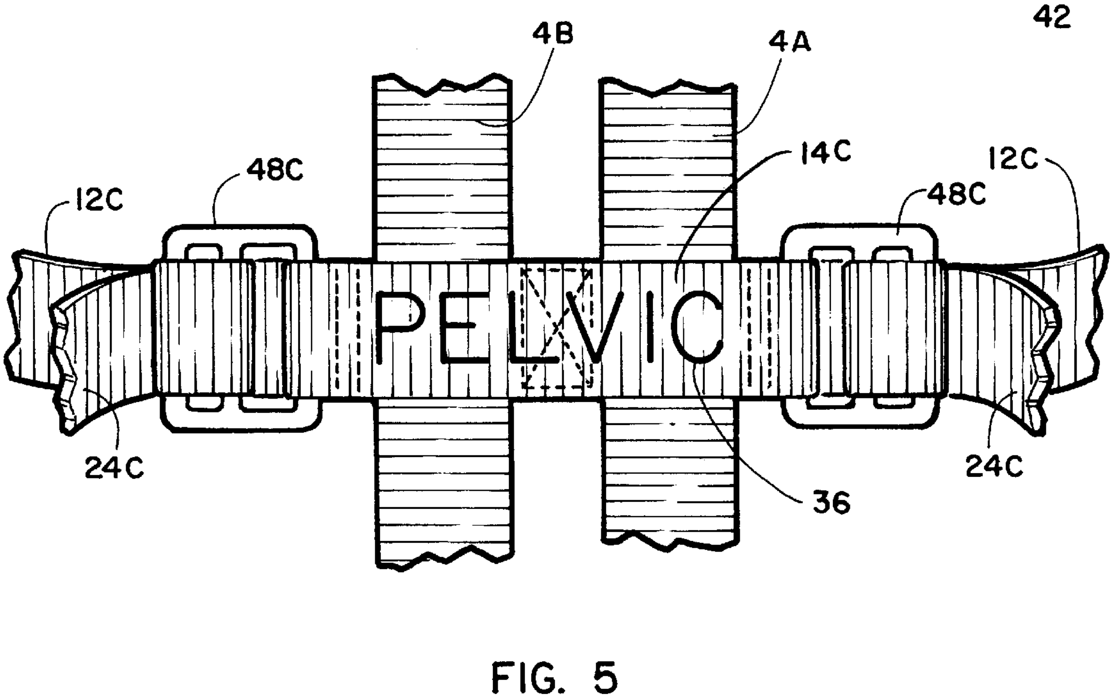
FIG. 5 is a detail of the assembly of a slideable spacer piece of the litter strapping device of FIG. 3 showing a legend printed on the slideable spacer piece with attached bilaterally extending straps and hardware.

FIG. 5 is a detail showing the assembly of a representative spacer piece 14*c* with the legend "PELVIC" 36*c* printed thereon to indicate the position relative to the body of subject 28 where the respective spacer piece and attached pair of bilaterally extending straps are to be placed during use. FIG. 5 also illustrates the threading of bilaterally extending straps 14*a* through buckle pair 48A to allow for adjustment of the effective length of the strap. Each spacer piece in the strapping device is preferably marked in like fashion with an appropriate legend. The head and leg ends of the longitudinally extending straps also bear appropriate legends to indicate the proper orientation of the invention strapping device with respect to body board 32 and the supine subject 28 thereon.

As shown in FIG. 3, the litter strapping device further has optional foot straps 56A–B with attached pair of cinching fasteners 50A–B and shoulder straps 58A–B with attached pair of cinching fasteners 50A–B. With the cinching fasteners disengaged, the foot straps and shoulder straps can be looped around the feet and shoulders of the subject (as shown) to further stabilize the subject in the litter.

Litter strapping device 40 is applied to Stokes basket 52 as follows. With the locking fasteners threaded onto the straps and the straps threaded through their respective buckles or cinching fasteners, device 40 is placed along the midline of the body of subject 28, utilizing the legends printed on the upper side of the spacer pieces and on the head and foot ends of the longitudinally extending straps in spaced apart relation as indicated on legends 36 printed on the upper side of the spacer pieces. The straps are freed from their respective attached containment strips and the locking fasteners are fastened around railing 54 of Stokes basked 52. The free end of each strap is then pulled to adjust the effective length of each strap. Preferably, this procedure of adjusting the effective length of the longitudinally extending and bilaterally extending straps is done by pairs to assure symmetry of the strapping device with respect to the midline of the subject's body.

In the embodiment of the litter strapping device shown in FIGS. 3 and 5, locking fasteners 42 are hook and latch fasteners wherein the hook 44 is opened by the operator depressing latch 46. When held in the open position, locking fastener 42 is hooked around the railing of the Stokes basket, and then pressure on the latch is released to lock the fastener around the railing.

Preferably the invention litter strapping device is manufactured to meet TRT requirements. For example, the straps are made of heavy duty polypropylene, canvas, cotton, or nylon webbing having a tensile strength in the range from about 2150 pounds to about 2700 pounds and the buckles and locking fasteners are made of heavy duty steel or aluminum. Preferably, as well, the materials in the device are selected to withstand sterilization conditions, such as high temperature and chemical means set forth by OSHA standards, as is known in the art, so that the device can be used repeatedly.

The litter used in transporting a patient from an inaccessible location is generally designed to accommodate a patient that has been fixedly bound to a backboard, if need be. In this case, the patient can be bound to the rigid board using an embodiment of the invention disclosed above as appropriate for binding or immobilization of a patient to such a board before the injured patient bound to the board is placed into the litter and secured therein using the invention litter strapping device. However, if the patient is suffering from a type of injury that does not involve spinal or neck injury, the patient is usually not bound to a rigid board for transport, but is placed directly into the litter (i.e., Stokes basket) and the invention litter strapping device is applied to prevent the patient from coming out of the litter during transport, even under the most rigorous of environmental (e.g., a high wind) or transport conditions (e.g., transport by helicopter or crane between ships at sea).

While the invention has been described in detail with reference to certain preferred embodiments thereof, it will be understood that modifications and variations are within the spirit and scope of that which is described and claimed.

What is claimed is:

1. A strapping device for fixedly binding a supine subject to a rigid board, said device comprising:

at least two lengthwise adjustable longitudinally extending straps having head ends, leg ends, and shoulder points, and being fixedly secured together at the leg ends and shoulder points, bilaterally extending straps being attached in pairs to the longitudinally extending straps, with pairs at the shoulder points and leg ends being fixedly attached, and additional pairs being attached to the longitudinally extending straps in spaced apart longitudinal relation between the leg ends and shoulder points, and cinching fasteners attached to free ends of the bilaterally extending straps for fixedly, but releasably binding the subject to the rigid board;

wherein the cinching fasteners are cooperatively engageable and the device is adapted to being passed over the subject supine on the board with the longitudinally extending straps attaching to the board at the head ends thereof, and the bilaterally extending straps being adapted to be passed around the subject and the rigid board and fastened together by cooperatively engaging the cinching fasteners.

2. A device according to claim 1 wherein the distance between the head ends and the shoulder points is adjustable.

3. The device according to claim 2 wherein the cinching fasteners are adjustable to tighten the bilaterally extending straps about the subject and the rigid board.

4. The device according to claim 1 wherein the cinching fasteners are cooperatively engageable and the device is adapted to being passed over the subject supine on the board with the longitudinally extending straps attaching to the board at the head ends thereof, and the bilaterally extending straps being adapted to be passed around the subject and the rigid board and fastened together by cooperatively engaging the cinching fasteners.

5. The device according to claim 1 wherein the two longitudinally extending straps each further have a foot holder attached to the leg end for receiving a foot of the subject.

6. The device according to claim 1 further comprising shoulder straps attached to the longitudinally extending adapted to adjustably loop about the two shoulders of the subject.

7. The device according to claim 1 wherein the pairs of bilaterally extending straps are slideably attached to the longitudinally extending straps so that the spaced apart longitudinal relation is adjustable.

8. The device according to claim 1 wherein the device is marked with a set of legends or symbols indicating points of proper placement of the pairs of slideable bilaterally extending straps along the length of the subject to be strapped to the rigid board.

9. The device according to claim 1 wherein each pair of bilaterally extending straps is slideably attached to the longitudinally extending straps by slide fasteners.

10. The device according to claim 9 wherein the bilaterally extending straps are marked with a set of legends or symbols indicating points of proper placement thereof along the length of the body of the subject.

11. The device according to claim 10 wherein the slide fasteners are spacer pieces and each legend or symbol identifies only one of the slideable spacer pieces and attached bilaterally extending straps for placement at or about the shoulders, chest, abdomen, pelvis or thigh region of the subject.

12. The device according to claim 10 wherein further legends or symbols identify the head and leg ends of the longitudinally extending straps.

13. The device according to claim 1 wherein the device is adapted for use in combination with a patient head block device fixedly attached to the rigid board to immobilize the head and/or neck of the subject.

14. The device according to claim 13 wherein the device is adapted to immobilize the remainder of the body of the subject in alignment with the immobilized head and/or neck.

15. The device according to claim 1 wherein the straps are made of heavy duty polypropylene, canvas, cotton, or nylon webbing.

16. The device according to claim 1 wherein the cinching fasteners are made of plastic, polypropylene, nylon, steel or aluminum.

17. The device according to claim 1 wherein the cinching fasteners are releasably engageable with one another by readily separable means.

18. The device according to claim 17 wherein said cinching fasteners are side release snap fasteners or pressure adhered hook and loop type fasteners.

19. The device according to claim 17 wherein the rigid board is provided with side railings or a plurality of spaced apart slots located pairwise along opposite sides of the board and the pairs of bilaterally extending straps and attached cinching fasteners are adapted to be threaded through the side railings or a corresponding pair of slots in the board with each bilaterally extending strap being fastened taut to itself by cooperative engagement of the attached releasably engageable cinching fastener so as to bind the subject to the board.

20. The device according to claim 19 wherein the rigid board is further provided with a head railing or head slot at the head portion thereof and wherein each longitudinally extending strap has an attached releasably engageable cinching fastener and is adapted to be threaded through the head railing or slot and fastened taut to itself by the releasably engageable cinching fastener.

21. The device according to claim 1 wherein the device is disposable.

22. The device according to claim 1 wherein the straps and cinching fasteners are designed to transport a patient weighing from about 40 pounds to about 350 pounds.

23. The device according to claim 1 wherein the device is adapted for emergency transport of an injured person by a technical rescue team.

24. The device according to claim 23 wherein the cinching fasteners are heavy duty steel or aluminum.

25. The device according to claim 23 wherein the tensile strength of each strap is at least 2500 pounds.

26. The device according to claim 23 wherein the device is further adapted to attach the rigid board to a Stokes basket having an upper railing and a lower railing.

27. The device according to claim 26 wherein the device is adapted to attach the straps about the lower railing of the Stokes basket.

28. The device according to claim 23 wherein the device can be sterilized for repeated use.

29. A strapping device for strapping a supine patient into a litter with attachment points, said device comprising:

at least two longitudinally extending straps, each having a head end, a foot end, and a shoulder point, being fixedly fastened together at the leg ends and shoulder points, pairs of bilaterally extending straps being fixedly attached to the foot ends and shoulder points of the longitudinally extending straps, additional pairs of bilaterally extending straps being attached between the foot ends and shoulder points of the longitudinally extending straps via slide fasteners, buckles attached to the longitudinally extending straps and bilaterally extending straps for adjusting the effective length of the straps, and locking fasteners attached to the longitudinally extending and bilaterally extending straps for releasably securing the straps to the attachment points of the litter.

30. The device according to claim 29 wherein the slide fasteners are slideable spacer pieces and at least four pairs of the bilaterally extending straps are slideably attached to the longitudinally extending straps via an individual slideable spacer piece slideably mounted on the longitudinally extending straps between the leg ends and the shoulder points.

31. The device according to claim 30 further comprising spacer pieces fixedly attached to the longitudinally extending straps at the leg ends and the shoulder points, each having a pair of the bilaterally extending straps attached thereto.

32. The device according to claim 29 wherein the device is marked with a set of legends or symbols indicating points of proper placement of the pairs of slideable bilaterally extending straps along the length of the subject to be strapped to the litter.

33. The device according to claim 29 wherein each pair of bilaterally extending straps is slideably attached to the longitudinally extending straps via an individual slideable spacer piece.

34. The device according to claim 33 wherein the spacer pieces are marked with a set of legends or symbols indicating points of proper placement of the pairs of slideable bilaterally extending straps along the length of the subject to be strapped to the litter.

35. The device according to claim 34 wherein each legend or symbol identifies only one of the slideable spacer pieces and attached bilaterally extending straps for placement at or about the shoulders, chest, abdomen, pelvis or thigh region of the subject.

36. The device according to claim 29 wherein at least one of the locking fasteners is attached to the jointure of the foot ends of the longitudinally extending straps via an intervening foot strap.

37. The device according to claim 29 wherein the locking fasteners are hook and latch fasteners.

38. The device according to claim 29 wherein the litter is a Stokes basket and the attachment points are along a railing surrounding the perimeter of the basket.

39. The device according to claim 29 wherein the straps are of polypropylene, canvas, cotton, or nylon and have a tensile strength in the range from about 2150 pounds to about 2700 pounds.

40. The device according to claim 39 wherein the buckles and locking fasteners are made of steel or aluminum and has a tensile strength of about 3500 pounds.

41. The device according to claim 29 wherein the device can be sterilized for repeated use.

42. The device according to claim 29 wherein the subject is secured to a backboard for immobilization before being placed in the litter and the device secures the subject on the backboard into the litter.

43. The device according to claim 29 wherein the device further comprises lengthwise adjustable foot loops attached to the longitudinally extending straps.

44. The device according to claim 29 wherein the device further comprises lengthwise adjustable shoulder loops with releasably engageable cinching fasteners for attaching around the shoulders of the subject in the litter.

45. The device according to claim 29 further comprising containment strips attached to the bilaterally extending straps and longitudinally extending straps for holding the straps in folded-up position.

* * * * *